United States Patent
Knapp et al.

(10) Patent No.: US 10,493,177 B2
(45) Date of Patent: Dec. 3, 2019

(54) SOLID STATE FRAGRANCING

(71) Applicants: Impact Products, LLC, Toledo, OH (US); ULTRATECH POLYMERS, INC., Cuyahoga Falls, OH (US)

(72) Inventors: Dennis Knapp, Toledo, OH (US); Anthony N. Kerkimis, Akron, OH (US); Nicholas A. Kerkimis, Akron, OH (US)

(73) Assignees: IMPACT PRODUCTS, LLC, Toledo, OH (US); ULTRATECH POLYMERS, INC., Cuyahoga Falls, OH (US)

( * ) Notice: Subject to any disclaimer, the term of this patent is extended or adjusted under 35 U.S.C. 154(b) by 428 days.

(21) Appl. No.: 15/404,299

(22) Filed: Jan. 12, 2017

(65) Prior Publication Data

US 2018/0193511 A1    Jul. 12, 2018

(51) Int. Cl.

| A61K 8/00 | (2006.01) |
| A61K 8/18 | (2006.01) |
| A61Q 13/00 | (2006.01) |
| A61L 9/12 | (2006.01) |
| A61L 9/012 | (2006.01) |
| B60H 3/00 | (2006.01) |
| A61L 9/04 | (2006.01) |

(52) U.S. Cl.
CPC ............... *A61L 9/12* (2013.01); *A61L 9/012* (2013.01); *A61L 9/042* (2013.01); *B60H 3/0028* (2013.01); *A61L 2209/15* (2013.01)

(58) Field of Classification Search
CPC .......... A61L 9/12; A61L 9/042; B60H 3/0028
USPC .......................................................... 512/1
See application file for complete search history.

(56) References Cited

U.S. PATENT DOCUMENTS

| 1,331,018 A | 2/1920 | Luthy |
| 1,336,495 A | 4/1920 | Wohler |
| 1,420,741 A | 6/1922 | Peyton |
| 3,002,704 A | 10/1961 | Grossfeld |
| 3,017,117 A | 1/1962 | Klingler |
| 3,803,327 A | 4/1974 | Fujimaki |
| 3,837,574 A | 9/1974 | Curran |
| 4,459,710 A | 7/1984 | Keyes et al. |
| 4,480,341 A | 11/1984 | Richards |
| 4,480,342 A | 11/1984 | Jones |
| 4,530,118 A | 7/1985 | Richards |
| 4,678,684 A | 7/1987 | Sand |
| 4,759,510 A | 7/1988 | Singer |
| 4,888,231 A | 12/1989 | Angstadt |
| 4,925,102 A | 5/1990 | Jones et al. |
| 5,023,020 A | 6/1991 | Machida et al. |
| 5,071,704 A | 12/1991 | Fischel-Ghodsian |
| 5,381,984 A | 1/1995 | Hindsgual |
| 5,494,218 A | 2/1996 | Armand |
| 5,873,529 A | 2/1999 | Johnson |
| 6,055,679 A | 5/2000 | Goetz et al. |
| 6,207,274 B1 | 3/2001 | Ferenc et al. |
| 6,425,530 B1 | 7/2002 | Coakley |
| 6,688,551 B1 | 2/2004 | He et al. |
| D507,341 S | 7/2005 | Taylor |
| 7,093,773 B2 | 8/2006 | Kuiper |
| 7,499,632 B2 | 3/2009 | Granger et al. |
| 7,651,763 B2 | 1/2010 | Hutchings et al. |
| 7,682,575 B2 | 3/2010 | Hurwitz et al. |
| 7,723,284 B2 | 5/2010 | Mane et al. |
| 7,754,198 B2 | 7/2010 | Whitehead et al. |
| 8,007,707 B1 | 8/2011 | Brown et al. |
| 8,137,629 B2 | 3/2012 | Faber et al. |
| 8,170,405 B2 | 5/2012 | Harris |
| 8,919,662 B2 | 12/2014 | Sherwood |
| 9,085,438 B2 | 7/2015 | Wilkins et al. |
| 2001/0020001 A1 | 9/2001 | Zembrodt et al. |
| 2003/0189127 A1 | 10/2003 | Arendt et al. |
| 2004/0253285 A1 | 12/2004 | O'Leary et al. |
| 2006/0099168 A1* | 5/2006 | Corzani ................... A61K 8/88 424/70.17 |
| 2007/0000037 A1 | 1/2007 | Wolf |
| 2007/0023564 A1 | 2/2007 | Platt |
| 2007/0204388 A1 | 9/2007 | Zyskowski et al. |
| 2008/0070025 A1 | 3/2008 | Pavlin |
| 2008/0078780 A1 | 4/2008 | Sanger et al. |
| 2008/0092282 A1 | 4/2008 | Altmann et al. |
| 2008/0241091 A1 | 10/2008 | McGee et al. |
| 2009/0001213 A1 | 1/2009 | Looft |
| 2009/0004234 A1 | 1/2009 | Kessler et al. |
| 2009/0158512 A1 | 6/2009 | Stickler et al. |
| 2010/0025490 A1 | 2/2010 | Bushman et al. |
| 2010/0270415 A1 | 10/2010 | Eakin |
| 2011/0002878 A1 | 1/2011 | Lamoreaux |
| 2011/0296597 A1 | 12/2011 | Brown et al. |
| 2012/0091251 A1 | 4/2012 | Smith |
| 2012/0097790 A1 | 4/2012 | Wilkins et al. |
| 2012/0193442 A1 | 8/2012 | Broderick |
| 2013/0239313 A1 | 9/2013 | Schiedel et al. |
| 2014/0034773 A1 | 2/2014 | Rote |
| 2014/0076983 A1* | 3/2014 | Irwin ..................... E03D 13/005 239/6 |
| 2014/0076984 A1* | 3/2014 | Irwin ......................... A61L 9/12 239/6 |
| 2014/0076991 A1 | 3/2014 | Irwin et al. |
| 2014/0175212 A1 | 6/2014 | Andrei |
| 2014/0231373 A1 | 8/2014 | Mellin |
| 2014/0231568 A1 | 8/2014 | Mellin et al. |
| 2014/0353418 A1 | 12/2014 | Hagleitner |
| 2015/0069172 A1 | 3/2015 | Bricker |

FOREIGN PATENT DOCUMENTS

| GB | 1336495 A | 11/1973 |
| WO | 9115177 | 10/1991 |

OTHER PUBLICATIONS www.Freshsticks.com, website, Oct. 18, 2013.

* cited by examiner

*Primary Examiner* — Jessica Whiteley

(74) *Attorney, Agent, or Firm* — Shumaker, Loop & Kendrick, LLP; James D. Miller

(57) ABSTRACT

Fragrance control is provided by articles of manufacture including various solid state fragrancing objects, methods of using such objects, and systems that employ one or more such objects. The fragrancing object can be easy to manufacture, long lasting, provide fragrance that is consistently released over time, provide an indication to the user that the object needs to be replaced, and can hold a desired ratio of fragrance. The solid state fragrancing object can be coupled to an air vent to inconspicuously provide fragrance to a user in an environment, such as the interior of a vehicle.

23 Claims, 4 Drawing Sheets

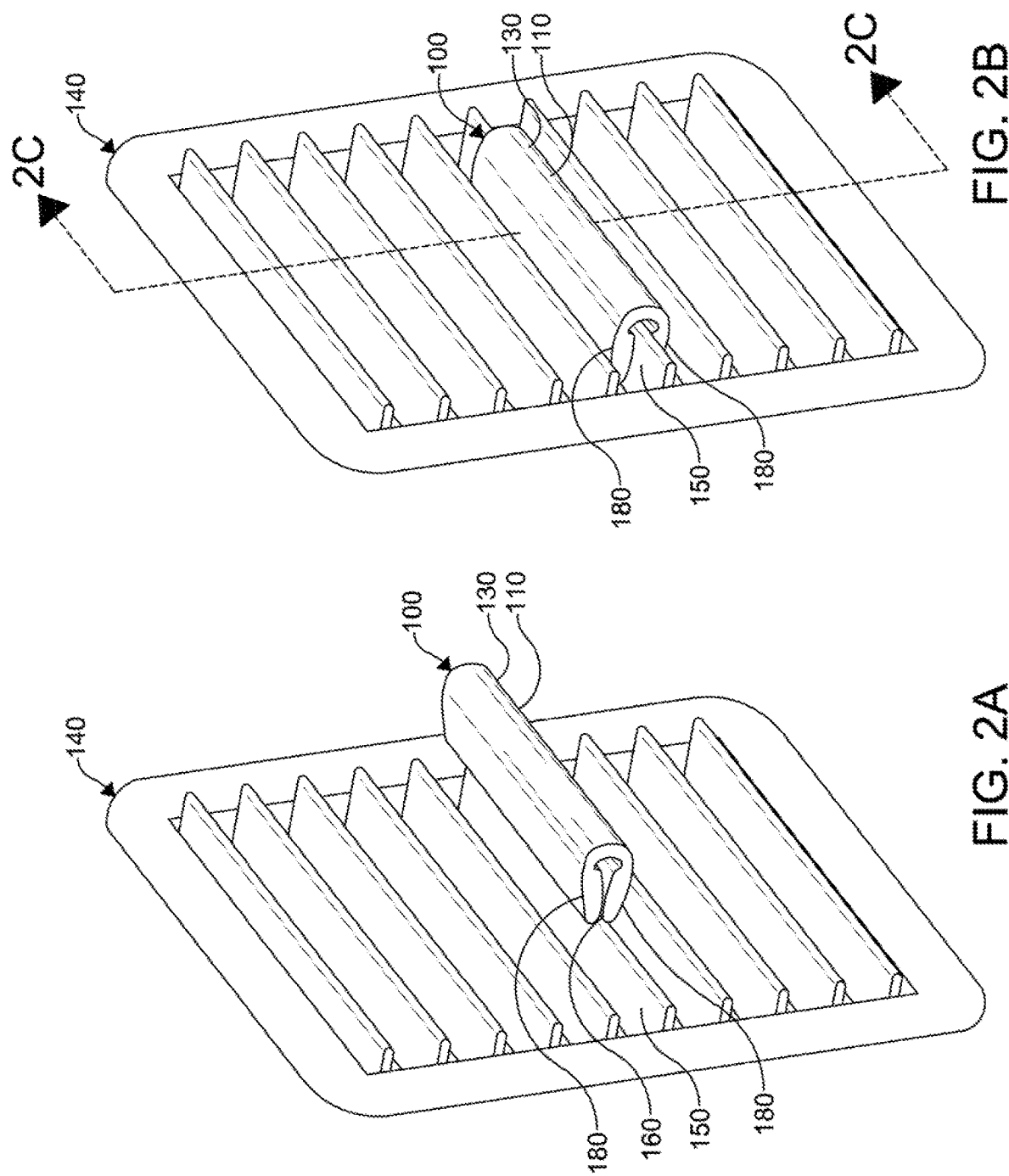

SOLID STATE FRAGRANCING

FIELD

The present technology relates to articles of manufacture, systems, and processes for fragrance control of one or more various environments. In particular, fragrance control can be employed in an environment, such as a vehicle interior, in order to provide a pleasant fragrance and/or to neutralize or reduce the impact of one or more unpleasant odors.

INTRODUCTION

This section provides background information related to the present disclosure which is not necessarily prior art.

It is often desirable to control the fragrance of certain environments, either to provide a particular fragrance as part of a particular experience or brand identity, for example, or to neutralize or reduce the impact of an unpleasant odor that may be encountered in the particular environment. Fragrance can be passively emitted into an environment by diffusion of a fragrancing component. Alternatively, an environment including a forced air heating, ventilation, and air conditioning (HVAC) system can actively circulate fragrance throughout the environment during operation of the HVAC system. As one example, fragrance control within a vehicle can provide an occupant with a more pleasant experience and can complement other aspects and perceptions of the environment, such as general cleanliness.

Various fragrancing objects are commonly used to mask or eliminate undesirable odors and emit a preferable scent. Many types of fragrancing objects are available, including those having liquid fragrances or fragrance oils, including plastic or paper-based objects containing a fragrance. Fragrancing objects may operate in various ways, including plug-in or spray mechanisms, and may emit or evaporate a fragrance over time. Certain devices having a fragrancing or deodorizing material absorbed into the device are configured to be disposed within a passenger compartment of a vehicle. For example, such devices can be hung from the rear-view mirror or from other locations.

Some ways of providing environmental fragrance control can exhibit one or more shortcomings. For example, some fragrancing objects are not capable of holding a desired amount or ratio of a fragrancing component, such as a fragrance oil, in comparison to other materials included in the fragrancing object, and may not be easy to manufacture or provide the desired performance. Some fragrancing objects do not provide an optimal release of fragrance over a long period of time and do not provide scent coverage throughout an environment. Other fragrancing objects can obstruct the view of an automobile occupant or operator, where hanging a fragrancing object from the rear-view mirror of a vehicle may even be illegal in particular cases. Certain fragrancing objects, including those containing fragrancing oils, can react with or mar vehicle interior surfaces, leaving unsightly residues, marks, or even compromise surface finishes, for example. Various fragrancing objects can also be aesthetically unpleasing and/or interfere with the styling, layout, and even operation of control surfaces within the vehicle.

It would be desirable to provide fragrance control including a solid state fragrancing object that is easy to manufacture, long lasting, provides fragrance that is consistently released over time, provides effective scent coverage for the interior environment of a vehicle, does not negatively affect a surface to which the fragrancing object is coupled, and which blends into the vehicle interior in an inconspicuous fashion while not interfering with operation of control surfaces within the vehicle.

SUMMARY

The present technology includes articles of manufacture, systems, and processes for fragrance control that use a solid state fragrancing object that is easy to manufacture, is long lasting, provides fragrance that is consistently released over time, and holds a desired ratio of fragrance.

In some embodiments, a solid state fragrancing object is provided that comprises a solid material, the solid material including about 10% by weight to about 40% by weight of a fragrance oil, about 40% by weight to about 70% by weight of a polyolefin elastomer elastomer, and about 5% by weight to about 20% by weight of a polyether block amide. The solid material can have a substantially constant cross-sectional area in a longitudinal dimension. The solid material can be formed as a unitary body or the solid material can be formed from multiple separate pieces that can be coupled, joined, or fitted in various ways. The solid material can be configured as an air vent, a louver of an air vent, or in a form that can be coupled to an air vent. The solid material, for example, can be configured to be coupled to the air vent by direct contact of the solid material with the air vent. To this end, the solid material can include a recess extending in the longitudinal dimension where the recess can be configured to receive a louver of the air vent. The substantially constant cross-sectional area of the solid material in the longitudinal dimension can be substantially U-shaped. The combination of the fragrancing oil, polyolefin elastomer, and the polyether block amide minimizes any negative effects of the fragrancing oil on a surface or finish directly contacted by the solid material.

In various embodiments, methods for fragrance control are provided where one or more solid state fragrancing objects are coupled to various features within an environment. One or more solid state fragrancing objects can be coupled to one or more portions of a forced air HVAC system in a vehicle. The solid material of the solid state fragrancing object can placed in direct contact with an air vent, where the solid material can be configured to slide, snap, or clip onto a louver of the air vent. Methods further include forming the solid material by extruding a fragrancing oil, polyolefin elastomer, and a polyether block amide to form a solid material having a substantially constant cross-sectional area in a longitudinal dimension.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is a perspective view of the first embodiment of the solid state fragrancing object approaching a louver of a vehicle air vent.

FIG. 2B is a perspective view of the first embodiment of the solid state fragrancing object directly coupled to the louver of the vehicle air vent.

DETAILED DESCRIPTION

Figure 1A:
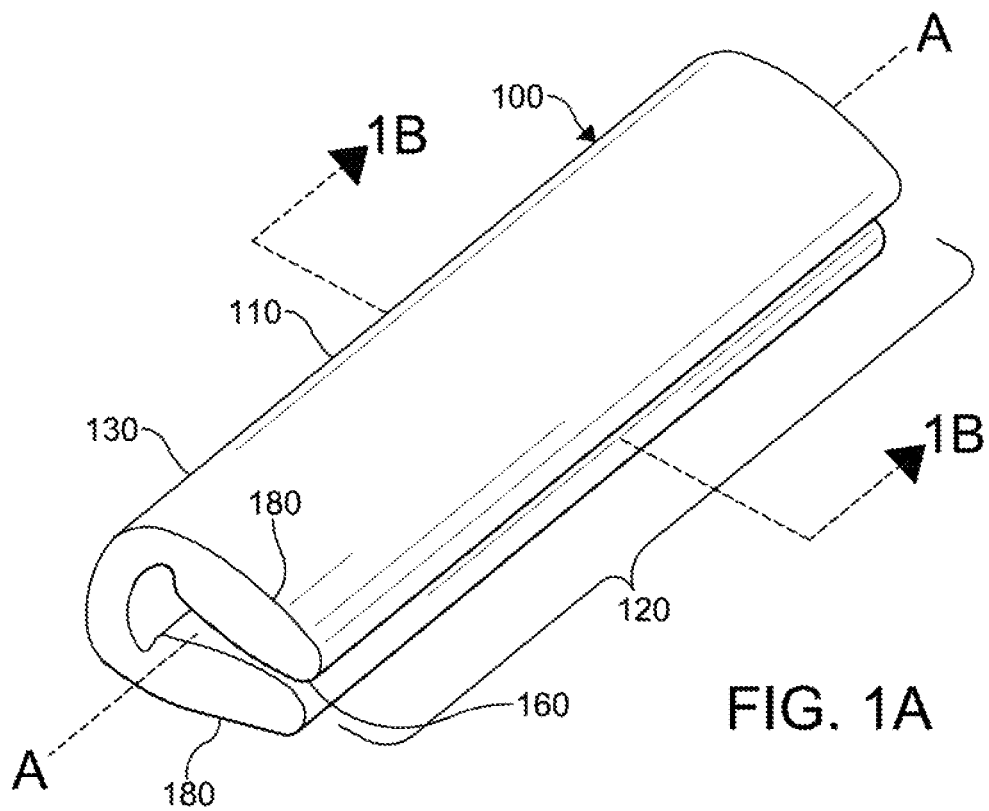
FIG. 1A is a perspective view of a first embodiment of a solid state fragrancing object according to the present technology.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. Except where otherwise expressly indicated, all numerical quantities in this description are to be understood as modified by the word "about" and all geometric and spatial descriptors are to be understood as modified by the word "substantially" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology relates to articles of manufacture including various solid state fragrancing objects, systems that employ such solid state fragrancing objects, and methods of using and making such solid state fragrancing objects. The solid state fragrancing object is easy to manufacture, long lasting, provides fragrance that is consistently released over time, and holds a desired amount of fragrance. In particular, one or more fragrance components are released or volatilized over time to provide an environment, such as the passenger compartment of a vehicle, with a desired fragrance. A solid state fragrancing object according to the present technology will not negatively affect a surface to which the fragrancing object is coupled. In particular, direct contact between the solid state fragrancing object and a surface, such as a plastic air vent louver, will not react with, mar, or compromise the surface finish. The solid state fragrancing object can include a solid material, where the solid material includes a fragrance oil, a polyolefin elastomer, and a polyether block amide. The solid material can have a substantially constant cross-sectional area in a longitudinal dimension. For example, the solid material can be formed by extrusion through a die configured to provide a desired cross-sectional design.

The solid state fragrancing object comprises a solid material, where the solid material can be described as in a solid phase at room temperature. For example, the solid material can be flexible, resilient, and/or rubbery at room temperature, but the solid material does not flow or run like a liquid or gel. The solid material can be elastic, where the solid material is compressible and deformable, and able to return to an original shape following compression, deformation, or stretching. The solid material can have a substantially constant cross-sectional area in a longitudinal dimension. For example, the longitudinal dimension of the solid material can represent a length where a transverse dimension substantially perpendicular to the longitudinal dimension can represent a height and a width of the solid material. In certain embodiments, the substantially constant cross-sectional area can relate to the shape of an extruder die or head used to form the solid material by an extrusion process.

The solid material can be configured with a surface area to volume ratio from about 0.5:1 to about 50:1. The surface area to volume ratio is the amount of surface area per unit volume of the solid material, where the surface area is the amount of surface area exposed to air. The ratios provided herein are denoted as surface area:volume, but can also be written as (surface area)/(volume) or as a numerical value having units of inverse distance, where the distance (d) can be meters, inches, etc. I.e., about 0.5:1 to about 50:1 can be written as about 0.5 $d^{-1}$ to about 50 $d^{-1}$. The surface area to volume ratio of the solid material can be tailored along with a particular emission rate of a fragrance oil, where generally increasing the surface area to volume ratio can increase an amount of the fragrance oil emitted for a given time from the solid material.

The solid material can be formed in various shapes and sizes. The solid material can be formed as a unitary body. By unitary body, it is meant that the solid material is a single piece of material and does not include multiple pieces coupled together. In certain embodiments, the solid material can be configured for coupling to one or more portions of a forced air HVAC system. For example, the solid material can be configured as an air vent or configured as a louver of an air vent. In other embodiments, the solid material can be configured to be coupled to an air vent. Coupling to the air vent can further include coupling the solid material to a control knob of the air vent used to position one or more louvers of the air vent, including opening/closing the louvers and/or using the louvers to direct air flow. The solid material can also be configured as an air vent control knob, where the solid material can replace or cover an existing control knob. The solid material, furthermore, can be configured to be coupled to the air vent by direct contact of the solid material with one or more portions of the air vent. Where the solid material is configured with one more recesses extending in a longitudinal dimension of the solid material, the one or more recesses can be configured to receive one or more louvers of an air vent. In certain embodiments, such as where the solid material has a substantially constant cross-sectional area in a longitudinal dimension, the substantially constant cross-sectional area can be substantially U-shaped. The open end of the U-shape can be configured as a recess that receives a louver of the air vent. By substantially U-shaped, it is understood that the cross-sectional area can vary in size, length, and thickness of the edges or arms and the bottom of the U, where the angle of the edges or arms relative to the open end of the U can vary from curving together, as per a horseshoe, to parallel, to spreading outward.

The solid state fragrancing object can be formed of one or more separate pieces that are assembled together and/or the fragrancing object may be assembled with other materials or coupled to other components or materials. For example, the solid material can be coupled to a holder or mount that is affixed to a surface within the environment. In some embodiments, the solid material can take the form of a rod, tube, blade, clip-on tube, slide-in blade, disk, cartridge, ornamental object, air vent or portion of an air vent, screen, or various air freshener shapes.

In some instances, it may be desirable to inconspicuously provide fragrance within an environment, such as the interior of a vehicle. Placing one or more fragrancing objects in an environment can interfere with the aesthetics or decor, especially where the fragrancing object is recognizable as such. Readily identifiable fragrancing objects may also be moved about the environment by a vehicle passenger, for example, and placed in a location that is less optimal for fragrance control. Such movement or repositioning of the fragrancing object may interfere with optimal fragrance coverage throughout the environment, providing over-fragranced areas and/or under-fragranced areas. Inconspicuously providing fragrance within an environment therefore can maintain optimal fragrance coverage, minimize any unsightly appearance of the fragrancing object, and minimize any interference of the fragrancing object with operation of the vehicle, including the view out of the vehicle and/or the access to various control surfaces within the vehicle. Accordingly, the present solid material can be configured to appear as a portion of a fixture within the environment. For example, the solid material can be configured in color and/or texture to complement, blend in, or match the color and/or texture of various portions of the interior of a vehicle. The solid material can also have a substantially muted or neutral color, such as a shade of gray, brown, tan, white, black, etc. in contrast to vibrant shades of red, yellow, orange, blue, green, etc. Examples include where the solid material is inconspicuously configured as an air vent, a louver of an air vent, or configured to be coupled to a louver of an air vent. Inconspicuously disposing one or more solid state fragrancing objects can also minimize theft or vandalism when the solid state fragrancing objects are used in a rental vehicle, a taxi, a bus, or various types of public transportation.

The solid material can be disposed within a line of sight of the user and yet remain inconspicuous. For example, as the solid material can be configured as at least a portion of a fixture in the environment, the solid material can appear as something it is not; i.e., where the solid material is not readily identifiable as a fragrancing object. The solid material can simply appear as a part or extension of the preexisting fixture. That is, the solid material can be within one's line of sight, but can be adapted to blend into or appear as if it has another function or purpose. The solid material can be configured as at least a portion of the fixture within the environment, where it can partially cover, completely cover, or extend part of the fixture. In certain embodiments, the solid material is configured as a portion of a forced air HVAC system, including one or more air vents, louvers, ducts, filters, fans or fan assemblies, etc. Air vents, duct work, or other portions of an HVAC system can have disposed thereon one or more solid state fragrancing objects. For example, the solid state fragrancing object can cover or provide a trim appearance of one or more louvers, fins, or vanes of an air vent, including where the solid state fragrancing object is directly clipped or snapped thereon.

The solid material can also be disposed out of the line of sight of the user. For example, the solid material can be placed inside or behind an air vent or other fixture that is not typically viewable within the environment. Other locations out of the line of sight include inside a duct, conforming to the shape of or replacing a portion of an air duct, and installation within parts of a forced air HVAC system, including coupling to or replacing vehicle cabin air filters, and coupling to heat exchangers. Again, the solid material can still be configured as at least a portion of the fixture within the environment, where it can partially cover, completely cover, or extend part of the fixture. In this fashion the solid state fragrancing object still appears as something else or part of something else, where a user would not readily identify the solid state fragrancing object as a fragrancing object or other type of air freshener.

In some cases, the solid material can be removably coupled to the fixture, thereby allowing the solid material to be easily replaced with either a solid material having a different fragrance oil or a new solid material when the solid state fragrancing object no longer emits a desired amount of fragrance. The solid state fragrancing object can also be removed to provide cleaning access or fixture repair, depending on the nature of the fixture to which it is coupled. Convenient means to removably couple the solid state fragrancing object to the fixture include various mounts, bases, adhesives, double-side tape, and various fasteners. Alternatively, the solid state fragrancing object can be configured to be directly coupled to the fixture, e.g., configured to clip or snap onto the fixture, or the solid state fragrancing object can have some type of integral retaining means that allows the solid state fragrancing object to directly fit into, onto, or over at least a portion of the fixture.

More than one solid state fragrancing object can be disposed in the environment on more than one fixture. More than one solid state fragrancing object can also be configured as multiple portions of the same fixture. For example, a plurality of solid state fragrancing objects can be disposed throughout the environment on various fixtures with a portion of the plurality of solid state fragrancing objects configured as portions of the same fixture. Arranging multiple solid state fragrancing objects in this manner can optimize fragrance coverage and scent mapping throughout the environment. Use of multiple solid state fragrancing objects also allows the solid state fragrancing objects disposed on different fixtures, or even the same fixture, to have different fragrance oils. Different fragrances can be mapped to provide a dynamic and changing scent experience based on an occupant's location in the environment. For example, certain areas of the environment can be provided with greater fragrance and/or a different fragrance compared to other areas of the environment. Other examples include where one or more air vents positioned for an operator of a vehicle have a solid state fragrancing object providing one type of fragrance oil and one or more air vents positioned for a passenger of a vehicle have a solid state fragrancing object providing another type of fragrance oil. Multi-passenger vehicles can have different solid state fragrance oils and/or intensities of fragrance disposed throughout different portions of the vehicle. Vehicles with separate occupant environments can thereby provide different fragrance experiences in each environment.

The solid material of the fragrancing object can include one or more fragrance oils. Various fragrance oils can be used, including natural and synthetic fragrance oils and blends thereof. The fragrance oil can also be described as an odorant, aroma, fragrance, or flavor that includes a chemical compound having a smell or odor. For example, a chemical compound can have a smell or odor when it is sufficiently volatile to be transported to the olfactory system in the upper-part of the nose. The fragrance oil can include such chemical compounds having a molecular weight of less than about 300 g/mol. The fragrance oil can include compounds derived from or mimicking various spices, foods such as fruits, perfumes, and fragrance oils including essential oils.

Fragrance oils, also known as aroma oils, aromatic oils, and flavor oils, can include single or blended synthetic compounds and/or natural essential oils. The fragrance oil can be diluted with a carrier oil or other solvent, such as various vegetable oils, mineral oil, or propylene glycol. Examples of various fragrance oils include those derived from: various mints including *Mentha arvensis*, peppermint, and spearmint; citrus oils from flowers and peels including orange, lemon, lime, and grapefruit; various barks and woods including cedar, sandalwood, sassafras, and cinnamon; various leaves, flowers, and fruits including *Eucalyptus globulus, Litsea cubeba*, clove (leaf), ylang ylang, patchouli, lemongrass, pine, rose, lavender, jasmine, sage, and rosemary; and various plant resins. Synthetic or chemically-modified versions of natural fragrance oils can also be used.

The fragrance oil can be loaded into the solid material in various amounts. For example, in some embodiments the solid material can include about 10% by weight of the fragrance oil to about 40% by weight of the fragrance oil. In various embodiments, the solid material can include at least about 20% by weight of the fragrance oil and in other embodiments the solid material can include at least about 25% by weight of the fragrance oil. Certain embodiments include where the solid material includes from about 15% by weight to about 35% by weight of the fragrance oil, other embodiments include where the solid material includes from about 20% by weight to about 35% by weight of the fragrance oil, and still further embodiments include where the solid material includes from about 25% by weight to about 30% by weight of the fragrance oil.

Various loadings of the fragrance oil can provide for a persistent and perceptible fragrance over a given period of time. For example, in some embodiments the fragrance oil can be perceptible for at least about 30 days within an environment of 100 cubic feet surrounding the solid state fragrancing object, and in other embodiments the fragrance oil can be perceptible for at least about 60 days within an environment of 100 cubic feet surrounding the solid state fragrancing object. By perceptible, it is meant that at least 50% of people on a test panel can detect the odor. For example, the environment containing the solid state fragrancing object and an environment without the solid state fragrancing object (as a reference) are presented to a group of panelists. In comparing the fragrance present in each environment, the panelists are asked to report if they can detect a difference between the environments. The test and perceptions by the panelists can be repeated as necessary to afford statistical relevance.

In addition to the fragrance oil, the solid material can comprise one or more various materials that are substantially solid at room temperature and maintain a substantially solid form when admixed with the fragrance oil. In this way, the solid state fragrancing object remains substantially solid and able to retain its shape when deployed within an environment. Suitable materials include various polymeric materials and porous materials that can absorb the fragrance oil to thereby limit or control the rate at which the fragrance oil is emitted from the solid state fragrancing object.

In some embodiments, the solid material can include a polyolefin elastomer and can include a polyether block amide. The solid material can have the appearance, feel, and behavior of rubber while the polyolefin elastomer and the polyether block amide content can allow flexible configuration and manufacturing of the solid material. The solid material can therefore exhibit properties similar to rubber and provide the advantages of plastic processing, in particular, where the polyolefin elastomer and a polyether block amide can be processed on conventional thermoplastic processing equipment. In certain cases, the solid material of the solid state fragrancing object can be an extrudate of the fragrance oil, the polyolefin elastomer, and the polyether block amide. Various means can be used to form an amalgam of the fragrance oil, the polyolefin elastomer, and the polyether block amide in forming the solid material. Embodiments include where the solid material has from about 10% by weight to about 40% by weight of the fragrance oil, about 40% by weight to about 70% by weight of the polyolefin elastomer, and about 5% by weight to about 20% by weight of the polyether block amide. Other embodiments include where the solid material has from about 20% by weight to about 30% by weight of the fragrance oil, about 50% by weight to about 60% by weight of the polyolefin elastomer, and about 10% by weight to about 15% by weight of the polyether block amide. Still further embodiments include where the solid material has from about 20% by weight to about 35% by weight of the fragrance oil, about 30% by weight to about 70% by weight of the polyolefin elastomer, and about 10% by weight to about 35% by weight of the polyether block amide.

The presence of certain amounts of the polyolefin elastomer and the polyether block amide in the solid material can provide benefits and advantages with respect to the fragrance oil. In particular, fragrance oils can react with or mar surfaces contacted by the fragrance oil, leaving unsightly residues, marks, and can even compromise a surface finish. Certain surfaces, including various plastic or painted surfaces, can be more prone to reacting or softening with a fragrancing oil, where negative effects can range from cosmetic to structural. Examples include where the plastic finish may be visibly altered to where the plastic itself is softened resulting in a compromised structure or warping. Other issues include where contact of the fragrancing oil with the surface results in an undesirable sticky surface that cannot be completely wiped off or cleaned. The present technology has surprisingly and unexpectedly found that the amounts of fragrance oil, polyolefin elastomer, and polyether block amide provided herein can effectively reduce or prevent the fragrancing oil from negatively affecting the surface to which the solid state fragrancing object is coupled. In particular, the solid material including the fragrancing oil, polyolefin elastomer, and polyether block amide can be placed in direct contact with various surfaces, including various plastic and painted surfaces, where the amounts of the polyolefin elastomer and polyether block amide minimize any negative impact of the fragrance oil with the surface. The properties of the polyolefin elastomer and polyether block amide unpredictably allow for loadings of fragrance oil that would otherwise compromise aspects of the surface, ranging from cosmetic to structural effects, if the fragrance oil itself was allowed to directly contact the surface or if the fragrance oil was mixed with a component other than the polyolefin elastomer and polyether block amide in forming the solid material. Use of the presently disclosed amounts of fragrance oil, polyolefin elastomer, and polyether block amide in the solid material therefore provide an advantage in conjunction with use of the fragrance oil in the present technology.

The polyether block amide used in the solid material can be obtained by polycondensation of a carboxylic acid polyamide with an alcohol termination polyether to provide a block copolymer with a sequence of polyamide and polyether segments. The block copolymer can include linear chains of relatively rigid polyamide and relatively soft polyether segments. Absorption and controlled release of volatile molecules (e.g., fragrance oils, fragrancing oils, etc.) can occur through the polyether phase of the material. The polyether block amide generally exhibits a good resistance to chemicals and some solvents. One source of a suitable polyether block amide includes PEBAX™ polyether block amides from Arkema Inc. (King of Prussia, Pa.). The polyether block amide can provide improved absorption and improved release of the fragrance component in comparison to other materials. Amounts of polyether block amide ranging from at least about 5% by weight to at least about 20% by weight can be included in the solid material. The polyether block amide can also be included in amounts from 10% by weight to about 35% by weight.

The polyolefin elastomer used in the solid material can include polyisobutylene, ethylene propylene rubber, and/or ethylene propylene diene monomer (M-class) rubber. Other examples include various copolymers of ethylene and another alpha-olefin, such as butene or octene; e.g., copolymers of ethylene-butene or ethylene-octene. POEs can be produced in various ways, including use of a metallocene catalyst, as is known in the art. Various polyolefin elastomers can be produced using monomer components of propylene, ethylene, butene, octene and/or hexene. Two examples of suitable polyolefin elastomers are Polyolefin Elastomer 999 Offgrade (an ethene-1-octene copolymer) and ENGAGE™ 8411 polyolefin elastomer (an ethylene-octene elastomer), both from Dow Chemical Co. (Midland, Mich.). Amounts of polyolefin elastomer ranging from at least about 1% by weight to at least about 40% by weight can be included in the solid material. The polyolefin elastomer can also be included in amounts from about 30% by weight to about 70% by weight.

The solid material can further include one or more additional materials or additives. Examples include various colorants, enzymes, odor neutralizers, sequestrants, counteractants, antioxidants, and UV blockers. Various processing additives can be included depending on the method of manufacture of the solid material, including various release agents, plasticizers, and curing agents.

In various embodiments, the solid state fragrancing object can be configured to have a certain surface area to volume ratio and can also be configured to have a certain surface area to environment volume ratio. As one example, the solid material can provide a particular surface area to volume ratio, where the ratio is tailored to particular applications. In some cases, the solid material can be configured with a greater surface area for a fixed volume to increase the emission rate of the fragrance component out of the fragrancing object to the environment; e.g., the fragrancing object can configured as a porous material or screen. In other cases, the solid material can be configured with a reduced surface area for a given volume to reduce the emission rate of the fragrance component out of the fragrancing object to the environment; e.g., the fragrancing object can be configured as a solid shape, such as a puck, block, or sphere. As another example, the solid material can have a surface area to environment volume ratio to provide a certain emission rate or amount of the fragrance component per environment volume. In certain cases, a square inch of fragranced surface area to environmental cubic foot volume ratio range can be about 0.01 to about 0.1. The solid material can also be tailored to have a surface area to volume ratio from about 0.5:1 to about 50:1, as described, in order to tailor an amount of the fragrance oil emitted per unit of time based on a particular emission rate.

As described, the solid material of the solid state fragrancing object can be coupled to a surface where there is direct contact between the solid material and the surface. The solid state fragrancing object can be configured in various ways to releasably couple to the surface by snapping, clipping, hooking, or engaging with the surface to maintain the position of the solid material on the surface. In some embodiments, a portion of the solid material can include an adhesive operable to couple the solid state fragrancing object to the surface. For example, the solid material can be in the form of a sheet, strip, panel, rod, or decal with adhesive on one side. The adhesive can be in the form of an adhesive backing that allows for peal-and-stick applications of the solid state fragrancing object.

The solid state fragrancing object can also include various additional features. The solid state fragrancing object can have one or more indicia on the solid material. Such indicia include various letters, numbers, and/or shapes to identify fragrance types, recycling codes, dates, etc. The solid material can also be scored or perforated facilitating subdividing the solid material into multiple pieces. For example, the solid material can be scored or perforated at regular intervals in order to adjust the amount of the solid state fragrancing object being deployed within the environment and/or to custom fit the solid material to a particular surface shape or size. Where the solid material is configured to fit an air vent louver, for example, scoring or perforations allow easy adjustment of the length of the solid material. Alternatively, the solid material can be simply cut or trimmed to fit (e.g., using scissors) depending on the configuration of the solid material. The solid material can further be enclosed by a barrier layer to limit emission of the fragrance oil until the solid state fragrancing object is ready to be deployed within the environment. Various barrier layers include single-ply and multi-ply polyolefin or polyamide films, bags, or containers; e.g., polypropylene, nylon, etc.

The solid state fragrancing object of the present technology can also comprise the solid material, with the solid material consisting essentially of the fragrance oil, the polyolefin elastomer, and the polyether block amide. By "consisting essentially of," it is meant that the solid material can include the fragrance oil, the polyolefin elastomer, and the polyether block amide and is open to other components that do not materially affect the basic and novel properties of the solid material. For example, the presence of any additional components in the solid material cannot affect the ability of the polyolefin elastomer and the polyether block amide to prevent or minimize surface damage by the fragrancing oil. The solid state fragrancing object can also comprise the solid material, with the solid material consisting of the fragrance oil, the polyolefin elastomer, and the polyether block amide. By "consisting of," it is meant that the solid material includes only the fragrance oil, the polyolefin elastomer, and the polyether block amide, and no additional materials, except for trace materials or contaminants resulting from typical manufacturing practices in the art or raw material grades available in the art.

The present technology also includes various methods for fragrance control of an environment. In some embodiments, a method is provided where a solid state fragrancing object is coupled to an air vent, where the solid state fragrancing object comprises a solid material, the solid material including a fragrance oil, a polyolefin elastomer, and a polyether block amide, the solid material having a substantially constant cross-sectional area in a longitudinal dimension. Coupling the solid state fragrancing object to the air vent can include coupling a plurality of solid state fragrancing objects to the air vent and/or to a plurality of air vents. At least one solid state fragrancing object can be coupled to each air vent. Where a plurality of solid state fragrancing objects are employed, the plurality of solid state fragrancing objects can include the same fragrance oil or can include different fragrance oils. In this way, the solid state fragrancing objects can be deployed throughout the environment so that perceptible fragrance zones substantially overlap or nearly overlap. The method can therefore minimize space in the environment where the various fragrance oils are not perceptible and can provide a substantially constant fragrance experience throughout the environment. The fragrance oils in the various solid state fragrancing objects can be the same or different, such that the system can be tailored to provide a continuous fragrance or different regional fragrances within the environment.

Methods of forming a solid state fragrancing object are provided. In various embodiments, the method can include providing a solid state fragrancing object comprising a solid material, the solid material including a fragrance oil, a polyolefin elastomer, and a polyether block amide, the solid material having a substantially constant cross-sectional area in a longitudinal dimension. The solid state fragrancing object can be modified by one or more of marking one or more indicia, scoring, perforating, die cutting, shaping, trimming, bending, braiding, and weaving. The solid material can be molded by injection molding, blow molding, rotational molding, or extrusion molding. In certain cases, the solid material is formed by extruding the fragrance oil, the polyolefin elastomer, and the polyether block amide. The method can include tumbling the fragrance oil, the polyolefin elastomer, and the polyether block amide and then extruding the fragrance oil, the polyolefin elastomer, and the polyether block amide to form the solid material having a substantially constant cross-sectional area in a longitudinal dimension. Extruding the solid material to form the solid state fragrancing object can include extruding the fragrance oil, the polyolefin elastomer, and the polyether block amide between about 140 degrees Centigrade to about 210 degrees Centigrade, and other embodiments can include temperatures between 140 degrees Centigrade and 180 degrees Centigrade, and still further embodiments can include temperatures between 160 degrees Centigrade to about 210 degrees Centigrade. Extruding the fragrance oil, the polyolefin elastomer, and the polyether block amide can be followed by cooling to form the solid material. For example, an extruder with various dies or extruder heads can be employed to provide various cross-sectional shapes to the resulting solid material. The fragrance oil, the polyolefin elastomer, and/or the polyether block amide can be in a liquid, semi-liquid, gel, or paste-like phase when present in the extruder, but become necessarily solid following extrusion to form the solid material. In particular, the fragrance oil, the polyolefin elastomer, and the polyether block amide can be mixed in the extruder and can include melt-mixing the fragrance oil, the polyolefin elastomer, and the polyether block amide in the extruder.

Extrusion can allow loading of the fragrance oil into the resulting solid material at levels that cannot be achieved using other means. For example, the extrusion process can provide a solid material that includes between 10% to about 40% by weight of the fragrance oil, where the polyolefin elastomer and the polyether block amide provide at least a portion to an entirety of the balance of the solid material. In some cases, the extrusion process can provide a solid material that includes between about 20% to about 30% by weight of the fragrance oil. Improved loading of the fragrance oil can be furthered by performing the extrusion process between about 160 to about 210 degrees Centigrade. In this way, loss of volatile fragrancing oils can be minimized.

In one embodiment, the solid state fragrancing object can be formed as follows. A fragrancing component in the form of a fragrancing oil, a polyolefin elastomer, and a polyether block amide can be tumbled together in a drum without the addition of heat. The tumbled fragrancing oil, polyolefin elastomer, and polyether block amide can then be melt-mixed and extruded, as described herein. Alternatively, the fragrance oil, the polyolefin elastomer, and the polyether block amide can be processed by other means, such as blending, pre-molding, molding, forming, and various post-forming processes. The solid material, including the fragrance oil, the polyolefin elastomer, and the polyether block amide, and any additives can be mixed and molded in a batch process or in a continuous process using an extruder, for example. Examples of post forming processes include marking one or more indicia, scoring, perforating, die cutting, shaping, trimming, bending, braiding, weaving, of the resulting solid material.

The present technology provides several advantages and benefits. In particular, the solid state fragrancing object is easy to manufacture, long lasting, and provides fragrance that is consistently released over time. The solid state fragrancing object thereby provides effective scent coverage for the interior environment of a vehicle. Notably, the solid material does not negatively affect a surface to which it is directly coupled, where the combination of the fragrance oil with the polyolefin elastomer and the polyether block amide surprisingly and unexpectedly prevents or minimizes marring of the surface or softening of paint or plastic finishes. The solid state fragrancing object can be configured to blend into the vehicle interior in an inconspicuous fashion while not interfering with operation of control surfaces within the vehicle. The solid state fragrancing object can be easily deployed within an environment by using a mount or holder or by directly coupling the objects to various fixtures or features within the environment, including various portions of a forced air HVAC system. There are no aerosols or liquids present following formation of the solid material, which can thereby minimize environmental impact and prevent any spills or drips in comparison with other fragrancing objects. For example, there is no possibility for oil based wick systems to leak or spill and no aerosol fallout creating a sticky or slippery surface. Likewise, there are no special storage or shipping requirements necessary with the present solid state fragrancing objects. The solid state fragrancing objects can be inconspicuously deployed in the environment to reduce theft and vandalism. Fragrance zones created by deploying a system for fragrance control can enhance the experience in the environment and reinforce a general perception of cleanliness. Multiple solid state fragrancing objects can also be mounted in various locations to optimize odor control efficacy and can be customized for environments ranging from small spaces to large spaces; e.g., personal vehicles to vans, buses, or other public transportation. Likewise, the fragrance oil can be tailored to fragrance type and strength preferences; e.g., men's fragrances, women's fragrances, brand identity, etc.

EXAMPLES

Figure 1B:
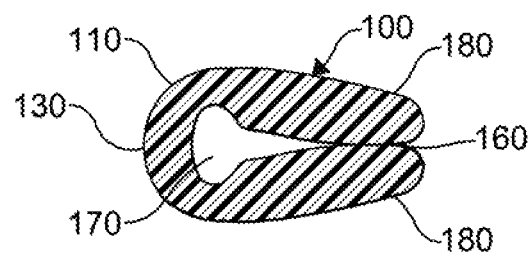
FIG. 1B depicts a cross-sectional view of the first embodiment of the solid state fragrancing object.
Figure 1C:
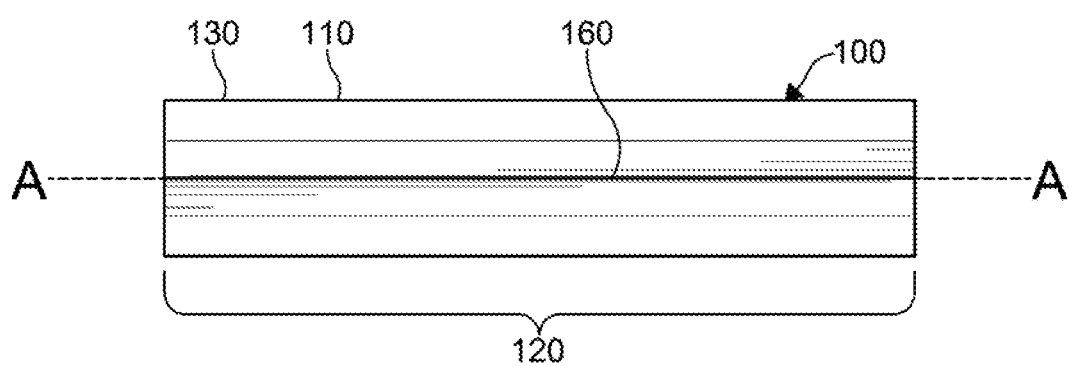
FIG. 1C is a side view along a longitudinal dimension of the first embodiment of the solid state fragrancing object.

With reference to FIGS. 1A-C, an embodiment of a solid state fragrancing object according to the present technology is shown at 100. The solid state fragrancing object 100 comprises a solid material 110 including a fragrance oil, a polyolefin elastomer, and a polyether block amide. The solid material 110 has a substantially constant cross-sectional area in a longitudinal dimension, as indicated by axis A. The longitudinal dimension denoted by axis A can define a length 120 of the solid material 110, where the length 120 is greater than other dimensions of the solid material 110 that are perpendicular to the axis A; e.g., a diameter of the solid material 110 or a height and a width of the solid material 110. The solid material 110 is formed as a unitary body 130, where the solid material 110 is a single, continuous piece that does not include multiple pieces coupled together.

Figure 2C:
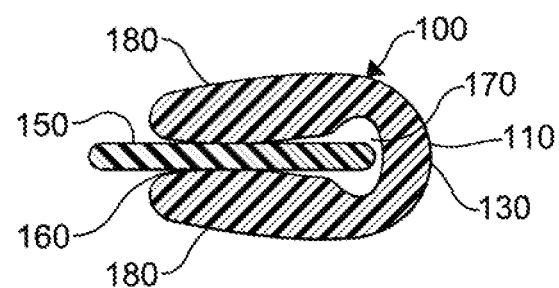
FIG. 2C depicts a cross-sectional view of the first embodiment of the solid state fragrancing object directly coupled and directly contacting the louver of the vehicle air vent.

With reference to FIGS. 2A-C, the solid material 110 of the solid state fragrancing object 100 is configured to be coupled to an air vent 140 of a force air HVAC system, such as that present in a vehicle. In particular, the solid material 110 is coupled to a louver 150 of the air vent 140, where the air vent 140 can include multiple louvers 150. FIG. 2A depicts the solid material 110 approaching the louver 150 and FIG. 2B depicts the solid material 110 coupled to the louver 150. Although not shown, more than one solid state fragrancing object 100 including more than one solid material 110 can be coupled to one or more louvers 150 of one or more air vents 140.

The solid material 110 includes a recess 160, where as shown, the recess 160 extends substantially parallel to the longitudinal dimension denoted by axis A along the solid material 110. The recess 160 has a profile 170 that can be configured along with various thicknesses of the solid material 110 to tailor the flexibility and resilience of the solid material 110 and to accommodate various sizes and shapes of louvers 150. In particular, the profile 170 can determine a clamping force of two edges 180 of the solid material 110 separated by the recess 160. The profile 170 of the recess 160 can further be tailored to engage different shapes and thicknesses of objects to be coupled thereto, including various shapes and thicknesses of louvers 150 of the air vent 140. Coupling the solid material 110 to the louver 150 includes direct contact of the solid material 110 with the louver 150 of the air vent 140, where the two edges 180 flex away from each other as the louver 150 is accommodated by the recess 160. The differences between FIG. 1B and FIG. 2C show in cross-section how the two edges 180 of the solid material 110 directly contact the louver 150 and provide a clamping force thereon to couple the solid material 110 to the air vent 140. As shown, the substantially constant cross-sectional area of the solid material 110 is substantially U-shaped, transitioning from a relative horseshoe likeness in FIG. 1B to where the edges 180 are somewhat parallel when the louver 150 is accommodated by the recess 160 in FIG. 2C.

The fragrance oil of the solid material 110 used in the solid state fragrancing object 100 includes a fragrance oil. The solid material 110 is an extrudate of the fragrance oil, the polyolefin elastomer, and the polyether block amide. Accordingly, the polyolefin elastomer and the polyether block amide serve to minimize any reaction between the fragrance oil and the louver 150 or any marring of the louver 150 by the fragrance oil when the louver 150 is formed of plastic and/or has a painted surface. The solid state fragrancing object 100 is therefore compatible with various air vents 140 formed of various materials, including those formed of plastic and/or having painted or coated surfaces, used in forced air HVAC systems of various vehicle environments.

Various examples of the solid state fragrancing object 100 including the solid material 110 have been produced that include about 10% by weight to about 40% by weight fragrance oil, about 40% by weight to about 70% by weight polyolefin elastomer, and about 5% by weight to about 20% by weight polyether block amide. Certain preferred examples include about 20% by weight to about 30% by weight of the fragrance oil, about 50% by weight to about 60% by weight of the polyolefin elastomer, about 10% by weight to about 15% by weight of the polyether block amide, and about 2% by weight to about 5% by weight of colorant. Black colorant can be used to match the solid state fragrancing object 100 to the louver 150 of the air vent 140, for example.

Figure 3:
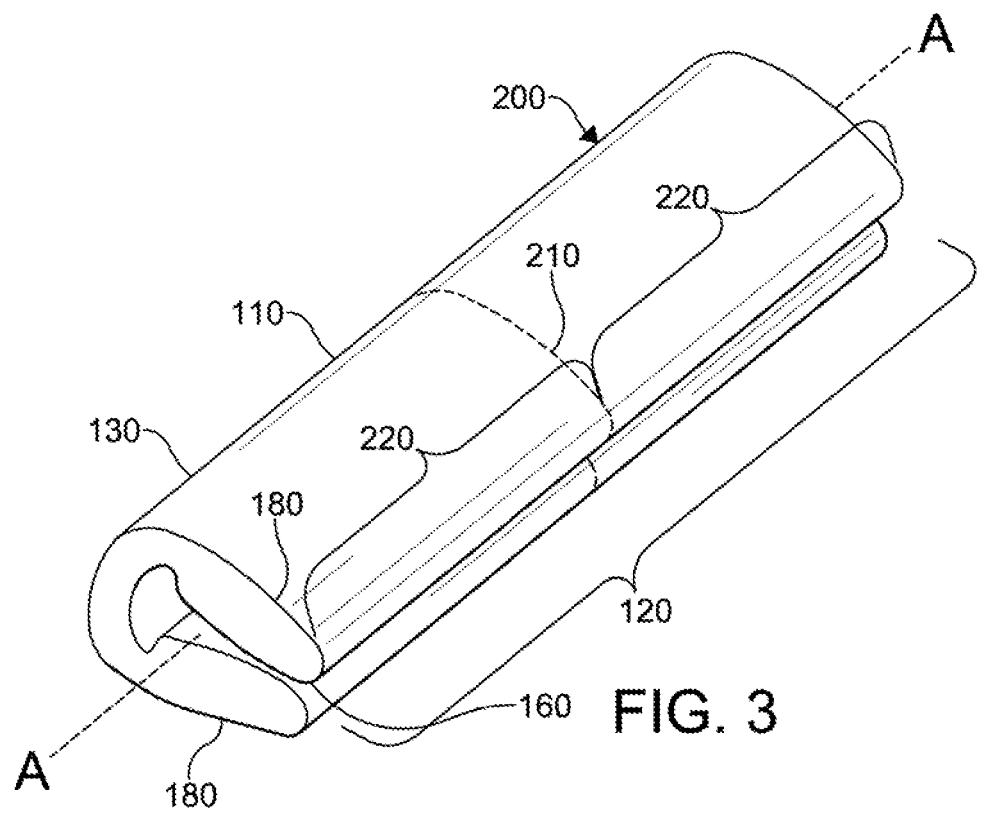
FIG. 3 depicts a perspective view of a second embodiment of a solid state fragrancing object according to the present technology.

With reference to FIG. 3, another embodiment of a solid state fragrancing object according to the present technology is shown at 200. The solid state fragrancing object 200 has the same features as shown for the solid state fragrancing object 100 in FIGS. 1A-C and FIGS. 2A-C, but includes indicia, scoring, or perforations denoted by 210. The indicia, scoring, and/or perforations at 210 can define sub-lengths 220 of the length 120 of the solid material 110. For example, indicia can indicate a location to cut the solid material 110 (e.g., using a blade or scissors) to provide a particular sub-length 220 and custom fit the solid state fragrancing object 200 for a particular installation. Scoring and perforations can be used to assist in separating the solid state fragrancing object 200 into the sub-lengths 220. Although only one indicia, scoring, or perforation location is shown at 210 in FIG. 3, multiple indicia, score marks, and/or perforations can be present on the solid state fragrancing object 200. For example, multiple indicia can mark defined sub-lengths 220 along the length 120 of the solid state fragrancing object 200; e.g., marking every centimeter or inch. Where the solid state fragrancing object 200 is configured to be inconspicuous within the environment, the indicia, scoring, or perforation shown at 210 can be faint or muted.

Figure 4:
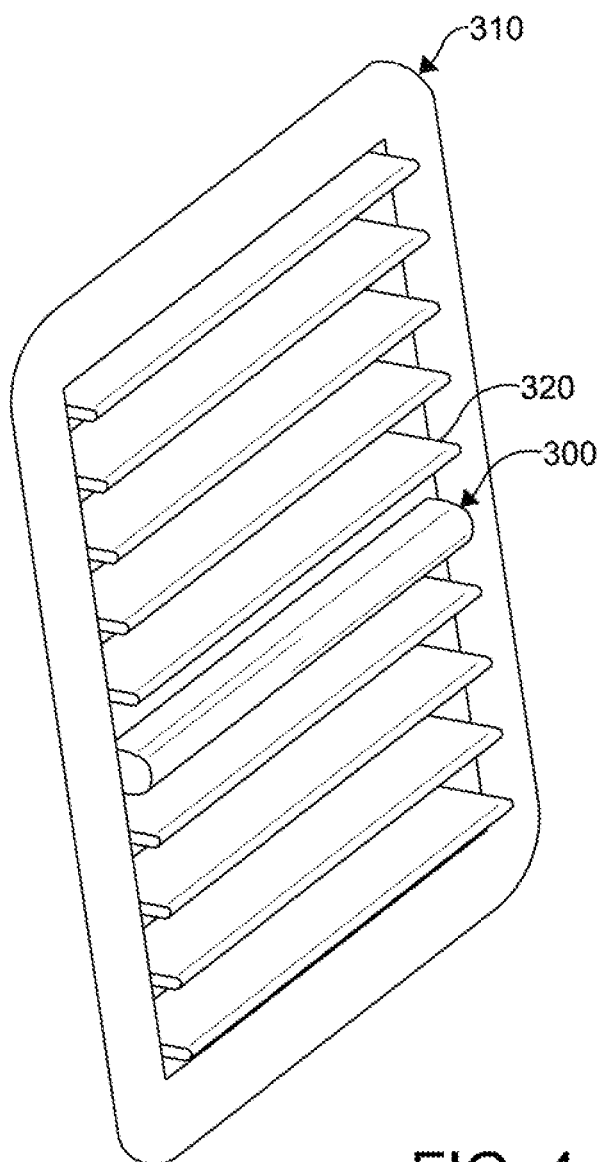
FIG. 4 depicts a perspective view of a third embodiment of a solid state fragrancing object according to the present technology.

With reference to FIG. 4, yet another embodiment of a solid state fragrancing object according to the present technology is shown at 300. The solid state fragrancing object 300 is configured as part of an air vent 310. The solid state fragrancing object 300 can operate as a control knob or be coupled to a control knob to operate other louvers 320 of the air vent 310. As shown, the solid state fragrancing object 300 can also function as a louver of the air vent 310. The embodiment of the solid state fragrancing object 300 shown is configured differently from the other louvers 320, but could be configured to match the other louvers 320 and replace one or more of the other louvers 320. In this way, the solid state fragrancing object 300 can comprise the entire air vent 310 or can comprise only various portions of the air vent 310.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A solid state fragrancing object comprising a solid material, the solid material including:
   about 10% by weight to about 40% by weight of a fragrance oil;
   about 40% by weight to about 70% by weight of a polyolefin elastomer; and
   about 5% by weight to about 20% by weight of a polyether block amide;
   wherein the solid material has a substantially constant cross-sectional area in a longitudinal dimension, the solid material includes a recess extending in the longitudinal dimension, the recess is configured to receive a louver of an air vent, the solid material includes two edges separated by the recess, the two edges contacting each other when the louver is not received in the recess, the solid material directly contacting the louver when the recess receives the louver of the air vent, the two edges providing a clamping force on the louver to couple the solid material to the air vent.

2. The solid state fragrancing object of claim 1, wherein the solid material is formed as a unitary body.

3. The solid state fragrancing object of claim 1, wherein the solid material is configured to be coupled to an air vent.

4. The solid state fragrancing object of claim 3, wherein the solid material is configured to be coupled to the air vent by direct contact of the solid material with the air vent.

5. The solid state fragrancing object of claim 1, wherein the substantially constant cross-sectional area in the longitudinal dimension is substantially U-shaped.

6. The solid state fragrancing object of claim 1, wherein the solid material includes from about 20% by weight to about 30% by weight of the fragrance oil, about 50% by weight to about 60% by weight of the polyolefin elastomer, and about 10% by weight to about 15% by weight of the polyether block amide.

7. The solid state fragrancing object of claim 1, wherein the solid material is an amalgam of the fragrance oil, the polyolefin elastomer, and the polyether block amide.

8. The solid state fragrancing object of claim 1, wherein the solid material has a surface area to volume ratio from about 0.5:1 to about 50:1.

9. The solid state fragrancing object of claim 1, wherein the solid material includes at least one indicium thereon.

10. The solid state fragrancing object of claim 1, wherein the solid material is one of scored and perforated.

11. The solid state fragrancing object of claim 1, wherein the solid material is enclosed by a barrier layer.

12. A solid state fragrancing object comprising a solid material, the solid material consisting essentially of:
   about 10% by weight to about 40% by weight of a fragrance oil;
   about 40% by weight to about 70% by weight of a polyolefin elastomer; and
   about 5% by weight to about 20% by weight of a polyether block amide;
   wherein the solid material has a substantially constant cross-sectional area in a longitudinal dimension, the solid material includes a recess extending in the longitudinal dimension, the recess is configured to receive a louver of an air vent, the solid material includes two edges separated by the recess, the two edges contacting each other when the louver is not received in the recess, the solid material directly contacting the louver when the recess receives the louver of the air vent, the two edges providing a clamping force on the louver to couple the solid material to the air vent.

13. A method for fragrance control comprising:
   coupling a solid state fragrancing object to an air vent;
   wherein the solid state fragrancing object comprises a solid material, the solid material including: about 10% by weight to about 40% by weight of a fragrance oil; about 40% by weight to about 70% by weight of a polyolefin elastomer; and about 5% by weight to about 20% by weight of a polyether block amide, wherein the solid material has a substantially constant cross-sectional area in a longitudinal dimension, the solid material includes a recess extending in the longitudinal dimension, the recess is configured to receive a louver of an air vent, the solid material includes two edges separated by the recess, the two edges contacting each other when the louver is not received in the recess, the solid material directly contacting the louver when the recess receives the louver of the air vent, the two edges providing a clamping force on the louver to couple the solid material to the air vent.

14. The method of claim 13, wherein coupling the solid state fragrancing object to the air vent includes coupling a plurality of solid state fragrancing objects to the air vent.

15. The method of claim 13, wherein coupling the solid state fragrancing object to the air vent includes coupling a plurality of solid state fragrancing objects to a plurality of air vents, wherein each air vent is coupled to at least one solid state fragrancing object.

16. The method of claim 15, wherein the plurality of solid state fragrancing objects include the same fragrancing component.

17. The method of claim 15, wherein the plurality of solid state fragrancing objects include different fragrancing components.

18. A method of forming a solid state fragrancing object comprising:

provides a mixture including about 10% by weight to about 40% by weight of a fragrance oil, about 40% by weight to about 70% by weight of a polyolefin elastomer, and about 5% by weight to about 20% by weight of a polyether block amide; and extruding the mixture to form the solid state fragrancing object, wherein the solid state fragrancing object has a substantially constant cross-sectional area in a longitudinal dimension, the solid material includes a recess extending in the longitudinal dimension, the recess is configured to receive a louver of an air vent, the solid material includes two edges separated by the recess, the two edges contacting each other when the louver is not received in the recess, the solid material directly contacting the louver when the recess receives the louver of the air vent, the two edges providing a clamping force on the louver to couple the solid material to the air vent.

19. The method of claim 18, wherein providing the mixture includes:

tumbling the polyether block amide with the fragrancing oil; and adding a polyolefin elastomer to the tumbled polyether block amide and fragrancing oil.

20. The method of claim 18, wherein extruding the mixture to form the solid state fragrancing object includes heating the mixture at a temperature between about 140 degrees Centrigrade and about 210 degrees Centrigrade.

21. The solid state fragrancing object of claim 1, wherein the substantially constant cross-sectional area of the solid material transitions from a substantially horseshoe shape to a substantially U-shape where the edges are substantially parallel when the recess receives the louver of the air vent.

22. The solid state fragrancing object of claim 1, wherein the longitudinal dimension defines a length of the solid material, where the length is greater than other dimensions of the solid material that are perpendicular to the longitudinal dimension.

23. The solid state fragrancing object of claim 1, wherein the solid material is elastic.

* * * * *